United States Patent
Heiliger et al.

[11] Patent Number: 5,994,561
[45] Date of Patent: Nov. 30, 1999

[54] PROCESS FOR THE PREPARATION OF AROMATIC MALEIMIDES

[75] Inventors: Ludger Heiliger, Neustadt/Weinstrasse; Rüdiger Herpich, Mannheim; Josef Käsbauer, Wermelskirchen; Friedrich-Wilhelm Ullrich, Bergisch Gladbach, all of Germany

[73] Assignee: Rhein Chemie Rheinau GmbH

[21] Appl. No.: 09/353,402

[22] Filed: Jul. 15, 1999

[30] Foreign Application Priority Data

Jul. 28, 1998 [DE] Germany ............ 198 33 912

[51] Int. Cl.$^6$ ................................ C07D 403/02
[52] U.S. Cl. ........................................... 548/522
[58] Field of Search ............................... 548/522

[56] References Cited

U.S. PATENT DOCUMENTS

| | | | |
|---|---|---|---|
| 4,130,564 | 12/1978 | Haug et al. | 260/326.26 |
| 4,154,737 | 5/1979 | Orphanides | 260/326.26 |
| 4,500,719 | 2/1985 | Oba et al. | 548/522 |
| 5,306,828 | 4/1994 | Adda et al. | 548/548 |

FOREIGN PATENT DOCUMENTS 2127025  1/1973  Germany .

*Primary Examiner*—Joseph K. McKane
*Attorney, Agent, or Firm*—Joseph C. Gil; Noland J. Cheung

[57] ABSTRACT

Aromatic maleimides can be prepared by reacting corresponding aromatic amines with maleic anhydride in the presence of a solvent mixture of halogenated hydrocarbon and a dipolar aprotic solvent, with the addition of acid and a polymerization inhibitor.

3 Claims, No Drawings

PROCESS FOR THE PREPARATION OF AROMATIC MALEIMIDES

FIELD OF THE INVENTION

The invention relates to an improved process for the preparation of aromatic maleimides by reaction of corresponding aromatic amines with maleic anhydride.

BACKGROUND OF THE INVENTION

The preparation of aromatic maleimides is known. Thus, for example, DE-A 2 127 025 describes a process for the preparation of aromatic maleimides which proceeds in two stages. In the first stage, the aromatic compound is added on to maleic anhydride in tetrahydrofuran as the solvent. In the second stage, a cyclization reaction of the maleic acid monoamide to give maleimide takes place, water being split off. Equimolar amounts of acetic anhydride and sodium acetate, based on the amide groups, must be employed in this reaction. According to DE-A 2 715 503, the cyclization reaction is carried out with triethylamine instead of with sodium acetate, and according to DE-A 2 719 903, a manganese/cobalt/lithium salt is employed for the cyclization reaction.

A disadvantage of the processes described above for the preparation of aromatic maleimides is that, for example, tetrahydrofuran is employed as the solvent, which requires considerable expenditure on appropriate safety measures because of its tendency to form peroxide and its low flash point. The situation is similar when triethylamine is employed, this having a comparably low flash point to that of tetrahydrofuran. The use of acetic anhydride is stoichiometric, and after the reaction gives equimolar amounts of acetic acid, which must be disposed of accordingly.

The solvent mixture of, for example, tetrahydrofuran, acetic acid, optionally residues of acetic anhydride and triethylamine, coupled with product residues and by-products, which is obtained after the reaction cannot be worked up without a relatively high technical expenditure, or cannot be recycled without appropriate purification.

SUMMARY OF THE INVENTION

The object of the present invention was thus to provide an economically and ecologically advantageous process for the preparation of aromatic maleimides which avoids the above-mentioned disadvantages and brings a correspondingly higher profitability and environment friendliness. The use of explosive solvents is to be avoided in the process according to the invention, and no stoichiometrically formed by-products which have to be disposed of accordingly should be obtained.

The present invention therefore provides a process for the preparation of aromatic maleimides of the formulae (I) to (IV).

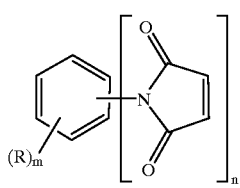

(I)

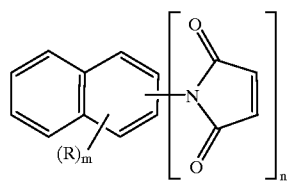

(II)

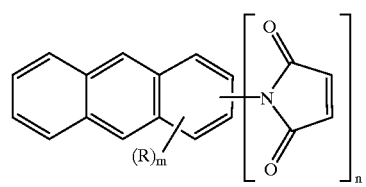

(III)

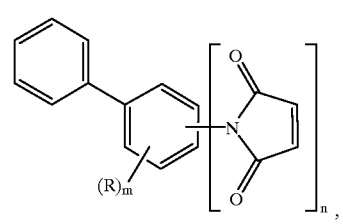

(IV)

wherein

R represents $C_1$–$C_{18}$-alkyl radicals, n denotes an integer from 2 to 4 and m represents integers from 0 to 3, which is characterized in that aromatic amines of the formulae (V) to (VIII)

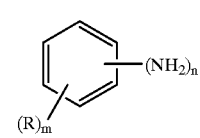

(V)

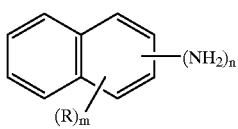

(VI)

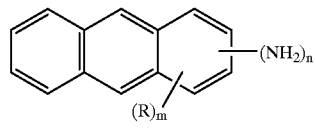

(VII)

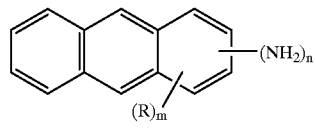

(VIII)

wherein

R, n and m have the abovementioned meanings, are reacted with maleic anhydride in the presence of a solvent mixture of a) 50 to 99 wt. % of an optionally halogenated hydrocarbon and b) 1 to 50 wt. % of a dipolar aprotic solvent with the addition of 0.1 to 10 wt. %, based on the maleic anhydride, of an acid and 0.01 to 2 wt. %, based on the maleic anhydride, of a polymerization inhibitor.

DETAILED DESCRIPTION OF THE INVENTION

In the abovementioned formulae, R preferably represents $C_1$- to $C_{12}$-, in particular $C_1$- to to $C_4$-alkyl radicals, n preferably represents 2–3 and m preferably represents 1–2.

Solvent mixtures which are preferably employed are those which comprise a) 70 to 99 wt. % of an optionally halogenated hydrocarbon and b) 1 to 30 wt. % of a dipolar aprotic solvent.

In the preferred embodiment of the process according to the invention, the reaction is carried out with the addition of 0.3 to 8 wt. % of an acid and 0.1 to 1 wt. % of a polymerization inhibitor.

Aromatic amines (V) to (VIII) which can be employed in the process according to the invention and are mentioned are, for example: phenylenediamines, toluylenediamines, naphthylamines, diaminonaphthalenes, aminoanthracenes, benzidine and diaminobenzidines, preferably 2,4-toluylenediamine and 1,3-phenylenediamine. The abovementioned aromatic amines can be employed both individually and as a mixture with one another.

Optionally halogenated hydrocarbons which can be employed are corresponding aliphatic, cycloaliphatic and aromatic hydrocarbons, which are mono- or polysubstituted by halogen atoms, such as fluorine, chlorine or bromine, and are present in liquid form at room temperature. For example, toluene, xylene, cyclohexane, isooctane and chlorobenzene, preferably toluene, xylene and chlorobenzene, are suitable for the process according to the invention. The hydrocarbons to be employed according to the invention can be employed both individually and as a mixture with one another.

Suitable dipolar aprotic solvents for the process according to the invention which may be mentioned are e.g.: N-methylpyrrolidone, dimethylsulfoxide, dimethylacetamide, dimethylformamide, formamide, ethylene glycols and propylene glycols and dialkyl carbonates, preferably N-methylpyrrolidone, dimethylformamide and ethylene glycol and propylene glycol, and N-methylpyrrolidone, dimethylformamide and dimethylacetamide are particularly preferred. These solvents can also be employed both individually and as a mixture with one another.

Possible acids are e.g.: mineral acids, such as hydrochloric acid, sulfuric acid and phosphoric acid, and Lewis acids, such as boron trifluoride, boron trichloride, iron trichloride, zinc dichloride and dialkyltin dialkanoates, acid anhydrides, such as diphosphorus pentoxide and trifluoromethanesulfonic acid anhydride, acid ion exchangers based on sulfonated styrene/divinylbenzene resins (e.g.Levatit®resins) and strong organic acids, such as para-toluenesulfonic acid, trifluoromethanesulfonic acid and trifluoroacetic acid. Hydrochloric acid, phosphoric acid, diphosphorus pentoxide, para-toluenesulfonic acid, trifluoromethanesulfonic acid and trifluoroacetic acid are preferred. para-Toluenesulfonic acid, phosphoric acid and di-phosphorus pentoxide are especially preferred.

Polymerization inhibitors which are to be mentioned are, above all, (polynuclear) phenols, and hydroquinone, para-methoxyphenol and 2,6-di-tert-butyl-para-methylphenol are preferred and hydroquinone and para-methoxyphenol are particularly preferred.

The acids and polymerization inhibitors mentioned can also be employed both individually and as a mixture with one another, it being possible for the most favourable mixing ratio to be determined in each case by corresponding preliminary experiments.

In the process according to the invention, the aromatic amines are reacted with maleic anhydride in the solvent mixture in the presence of the polymerization inhibitor at temperatures of 0 to 80° C., preferably at temperatures of 20 to 70° C. particularly preferably at 40 to 60° C., and the mixture is stirred until free amine can no longer be detected. The detection can be carried out using the conventional methods of monitoring reactions, such as by gas chromatography or thin layer chromatography. When free amine can no longer be detected, the acid is added. The reaction mixture is then heated to 90 to 140° C., preferably to 100 to 120° C., particularly preferably to 105 to 115° C. The heating phase lasts until the separation of water has ended, the solvent mixture being recycled.

The reaction in the process according to the invention can also be carried out in two stages, the aromatic amines being reacted with maleic anhydride in the solvent mixture in the presence of the polymerization inhibitor over a period of up to 8 hours, preferably 6 to 8 hours, in the first step at the stated temperatures. In the second stage, the reaction mixture of the first stage is metered into a solution of the catalyst acid in the solvent mixture at the stated temperatures over a period of up to 6 hours.

The reaction mixture is stirred at the abovementioned temperature for a further maximum of 6 hours, preferably 4–6 hours, until the separation of water has ended.

When the reaction has taken place, according to the invention the product is isolated by a procedure in which, after the mixture has been cooled to room temperature, the precipitate which has formed is filtered off, washed, dried and recrystallized. A further portion of the corresponding aromatic maleimide can be isolated from the mother liquor by distilling off the solvent and adding water.

The following examples are intended to illustrate the process according to the invention.

EXAMPLES

Example 1

Synthesis of 2,4-bis(maleimido)toluene

A mixture of 523 g toluene, 15 g N-methylpyrrolidone, 0.3 g hydroquinone and 98.1 g/1.0 mole maleic anhydride is heated to 60° C., while stirring, and 62 g/0.5 mole 2,4-toluylenediamine are metered in over a period of 3 hours. The mixture is subsequently stirred for 3 hours, 7.0 g para-toluenesulfonic acid are added and the contents of the flask are brought to the boiling point at 110° C., while stirring. After 8.25 hours, the azeotropic separation of water has ended and the solution is poured through a folded filter and left to cool to crystallize out.

The precipitate is filtered off with suction, dried at 70° C. in vacuo and comminuted.

Yield: 100 g (corresponds to 71% of theory). The substance was characterized by elemental analysis, TLC, IR and the melting point.

Melting point: 160–164° C.

Elemental analysis: $C_{15}H_{10}N_2O_4$(282.3 g/mole) calc.: C: 63.8 H: 3.6 N: 9.9 found: C: 64.2 H: 3.9 N: 9.9

TLC (mobile phase: ethanol, support material: silica gel): $R_f$ value:0.69 IR: 1700 $cm^{-1}$ stretching vibrations C=O 3100 cm$^{-1}$ stretching vibrations C$_{(arom.)}$—H 3500 cm$^{-1}$ stretching vibrations C$_{(aliphat.)}$—H

Example 2

Synthesis of 1,3-phenylenebis(maleimide)

A mixture of 196 g toluene, 26 g N-methylpyrrolidone, 0.15 g hydroquinone and 24.5 g/0.25 mole inaleic anhydride is heated to 60° C., while stirring, and 13.5 g/0.125 mole meta-phenylenediamine are metered in over a period of 1 hour. The mixture is subsequently stirred at this temperature for 2 hours.

This suspension is added dropwise to a boiling solution of 0.9 g para-toluenesulfonic acid in 15.5 g N-methylpyrrolidone and 118 g toluene over a period of 6 hours, while stirring. The water of reaction formed is distilled off azeotropically, the solvent mixture being recycled. The mixture is subsequently stirred for a further 2 hours and filtered. After cooling, 1,3-phenylenebis(maleimide) can be filtered off with suction, dried and powdered.

A further portion of product is isolated from the mother liquor by distilling off the toluene content from the solvent mixture, stirring the residue with 200 g water, filtering off the precipitate with suction and drying and powdering the solid.

For purification, the product is boiled in toluene, by-products are separated off by filtration at the boiling point and the solvent is distilled off.

Yield: 24.5 g (corresponds to 73% of theory). The substance was characterized by elemental analysis, TLC, IR and the melting point.

Melting point: 198–199° C.

Elemental analysis: C$_{14}$H$_8$N$_2$O$_4$ (268.2 g/mole) calc.: C: 62.7 H: 3.0 N: 10.4 found: C: 62.3 H: 3.2 N: 10.5

TLC (mobile phase: ethanol, support material: silica gel): R$_f$ value: 0.71 IR: 1600 cm$^{-1}$ stretching vibrations olef. C=C 1720 cm$^{-1}$ stretching vibrations C=O 2860 cm$^{-1}$ stretching vibrations C$_{(olef.)}$—H 3100 cm$^{-1}$ stretching vibrations C$_{(arom.)}$—H 3500 cm$^{-1}$ stretching vibrations C$_{(aliphat.)}$—H

We claim:

1. Process for the preparation of aromatic maleimides of the formulae (I) to (IV)

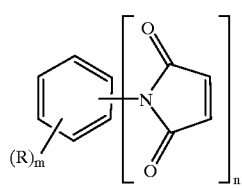
(I)

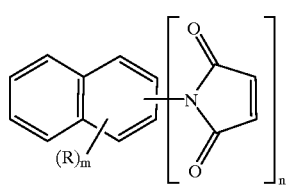
(II)

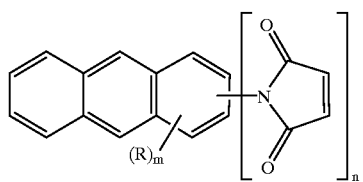
(III)

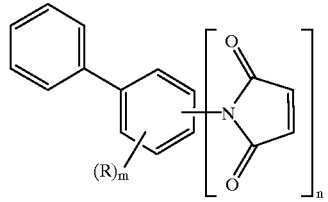
(IV)

wherein
R represents C$_1$–C$_{18}$-alkyl groups,
n denotes an integer from 2 to 4 and
m represents integers from 0 to 3,
wherein aromatic amines of the formulae (V) to (VIII)

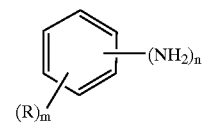
(V)

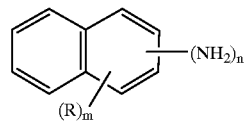
(VI)

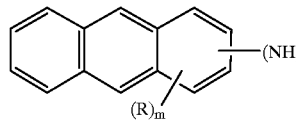
(VII)

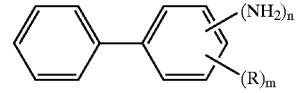
(VIII)

wherein
R, n and m have the abovementioned meanings,
are reacted with maleic anhydride in the presence of a solvent mixture of
a) 50 to 99 wt. % of a halogenated hydrocarbon and
b) 1 to 50 wt. % of a dipolar aprotic solvent
with the addition of 0.1 to 10 wt. %, based on the maleic anhydride, of an acid and 0.01 to 2 wt. %, based on maleic anhydride, of a polymerization inhibitor.

2. Process according to claim 1, wherein the solvent mixture comprises 70 to 99 wt. % of an optionally halogenated hydrocarbon and 1 to 30 wt. % of a dipolar aprotic solvent.

3. Process according to claim 1, wherein the reaction is carried out with the addition of 0.3 to 8 wt. % of an acid and 0.1 to 1 wt. % of a polymerization inhibitor, in each case based on the maleic anhydride employed.

* * * * *